United States Patent [19]

Sandhaus

[11] Patent Number: 4,967,949
[45] Date of Patent: Nov. 6, 1990

[54] APPARATUS FOR EFFECTING OCCLUSION OF THE VAS DEFERENS

[75] Inventor: Jeffrey J. Sandhaus, Palisades, N.Y.

[73] Assignee: Vastech Medical Products Inc., New Brunswick, N.J.

[21] Appl. No.: 326,299

[22] Filed: Mar. 21, 1989

Related U.S. Application Data

[63] Continuation-in-part of Ser. No. 884,417, Jul. 11, 1986, abandoned.

[51] Int. Cl.⁵ .................................................. A61B 17/00
[52] U.S. Cl. ...................................... 227/176; 227/19; 606/139; 606/142; 606/143
[58] Field of Search ..................... 606/139, 142, 143; 227/19, 121, 126

[56] References Cited

U.S. PATENT DOCUMENTS

| | | | |
|---|---|---|---|
| 4,299,224 | 11/1981 | Noiles | 606/143 |
| 4,325,376 | 4/1982 | Klieman et al. | 606/143 |
| 4,380,238 | 4/1983 | Colucci et al. | 606/135 X |
| 4,394,864 | 7/1983 | Sandhaus | 606/142 X |
| 4,430,997 | 2/1984 | DiGiovanni et al. | 606/143 |
| 4,448,193 | 5/1984 | Ivanov | 606/143 |
| 4,452,376 | 6/1984 | Klieman et al. | 606/142 X |
| 4,492,232 | 1/1985 | Green | 606/143 |
| 4,500,024 | 2/1985 | DiGovanni et al. | 227/19 |
| 4,616,651 | 10/1986 | Golden | 606/142 |
| 4,635,634 | 1/1987 | Santos | 606/142 |

Primary Examiner—Paul A. Bell
Attorney, Agent, or Firm—Lerner, David, Littenberg, Krumholz & Mentlik

[57] ABSTRACT

Apparatus for implanting closable locking clips to effect the percutaneous occlusion of target vessels is disclosed, including a pair of pivotable jaws defining a clip retaining cavity, a clip moving slide for sliding a locking clip from a retracted position remote from the clip retaining cavity to an actuated position with the clip retaining cavity, and a camming surface operatively disposed within the clip retaining cavity so that upon slidable movement of the locking clip from the retracted position to the actuated position the camming surface causes at least partial closure of the locking clip therein.

47 Claims, 16 Drawing Sheets

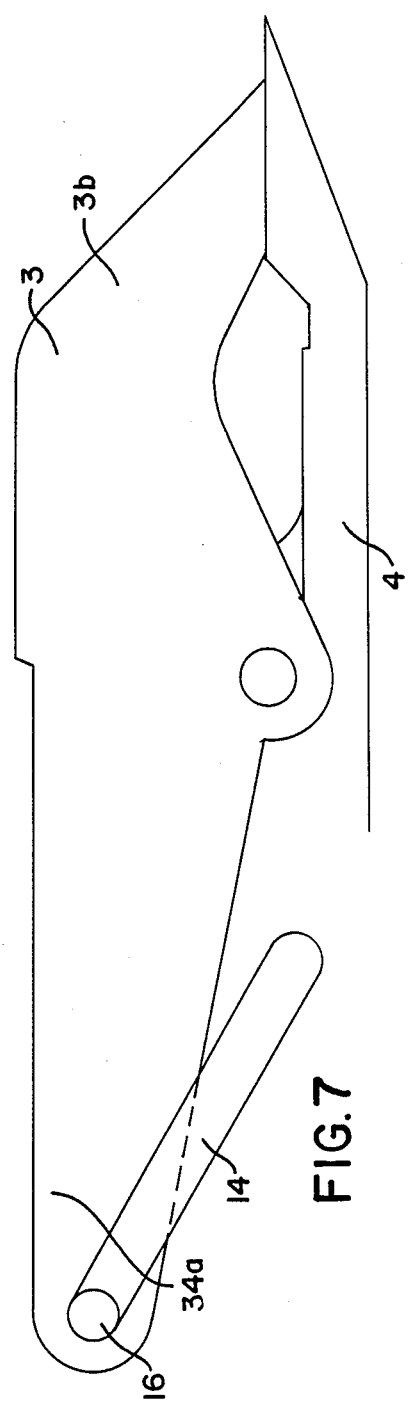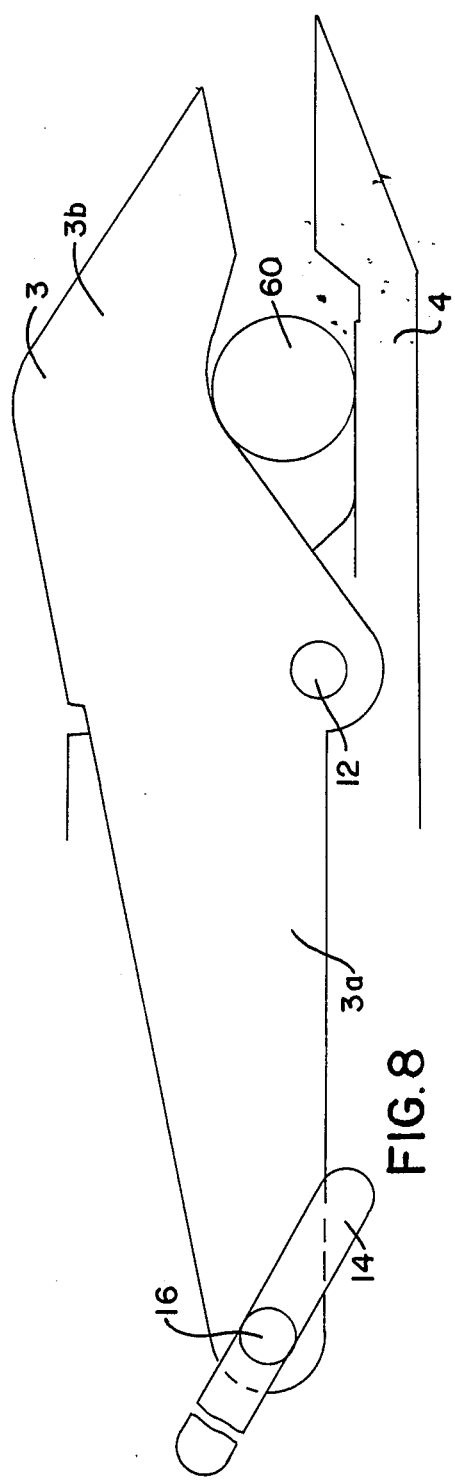

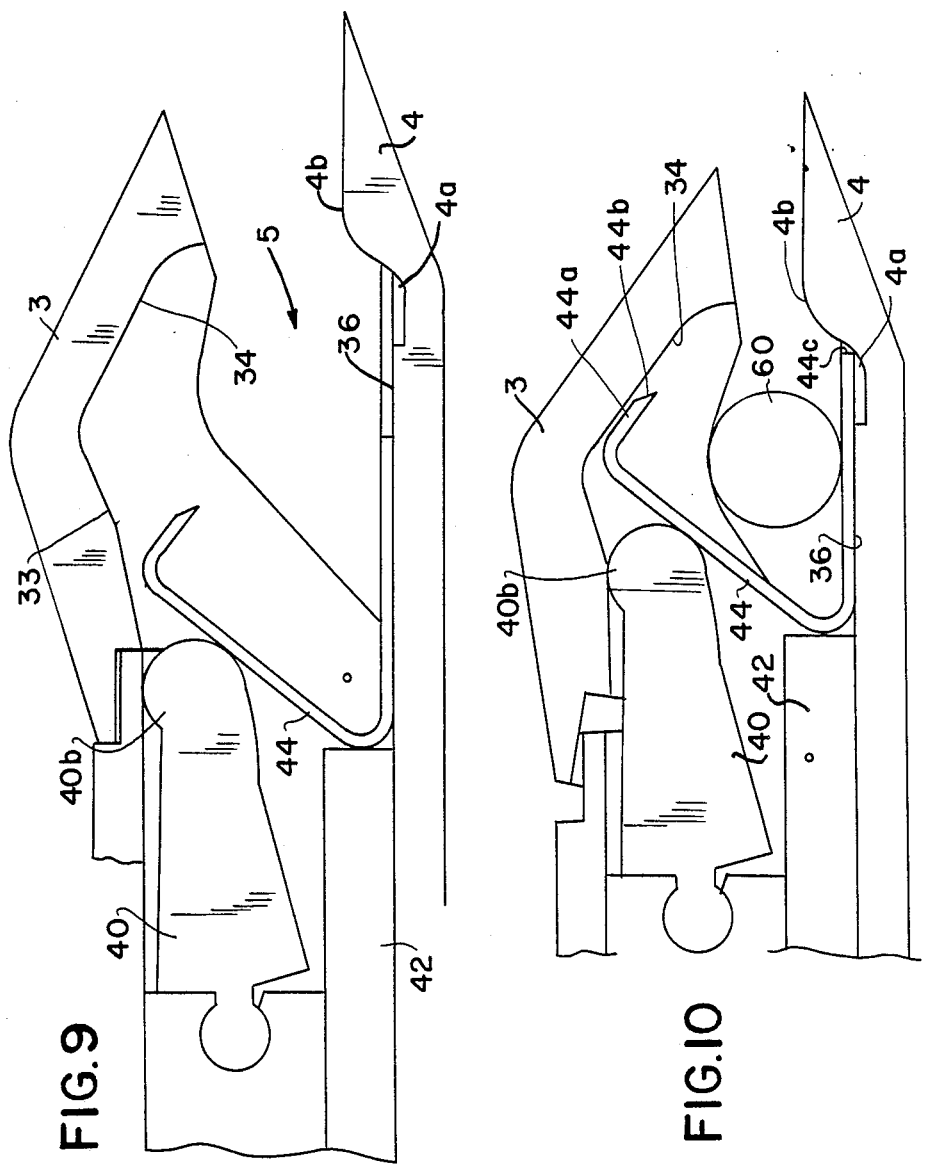

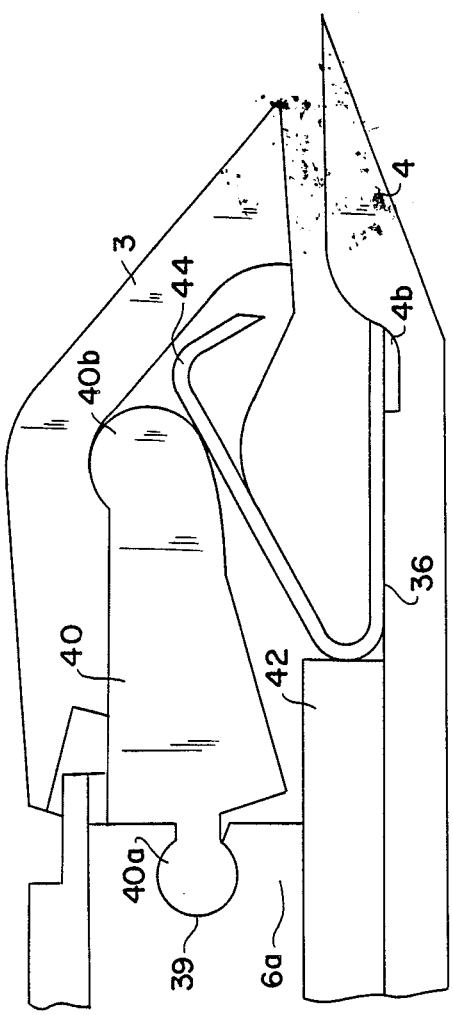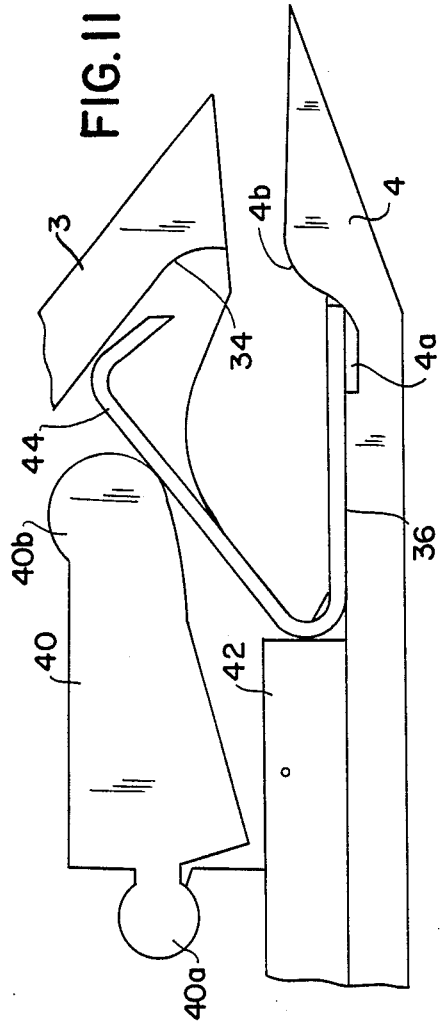

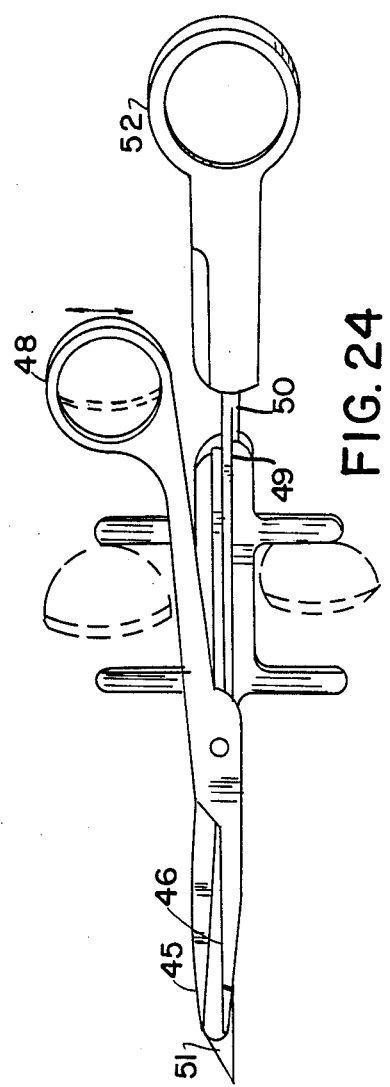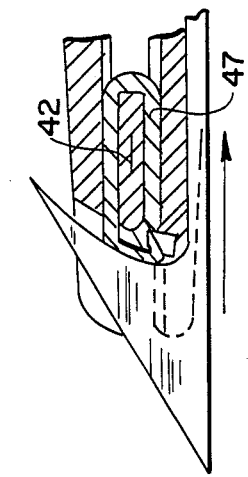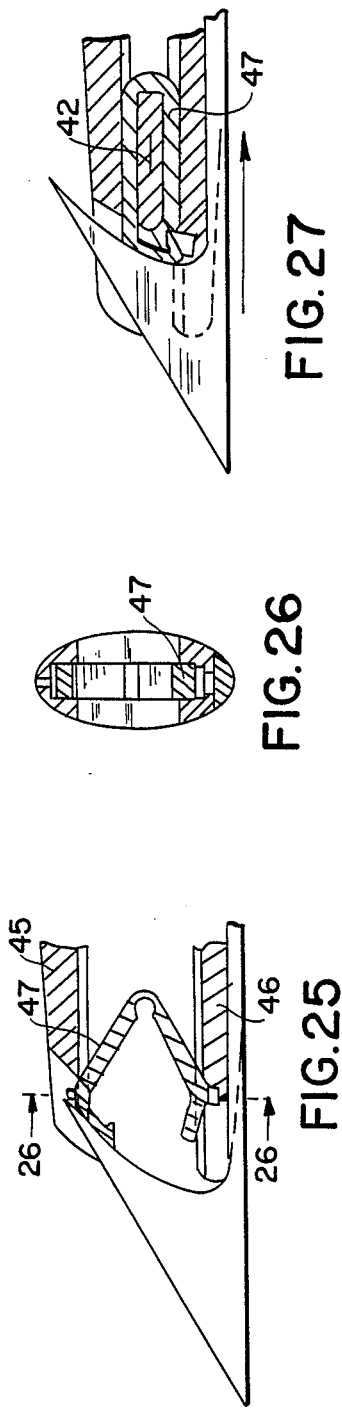

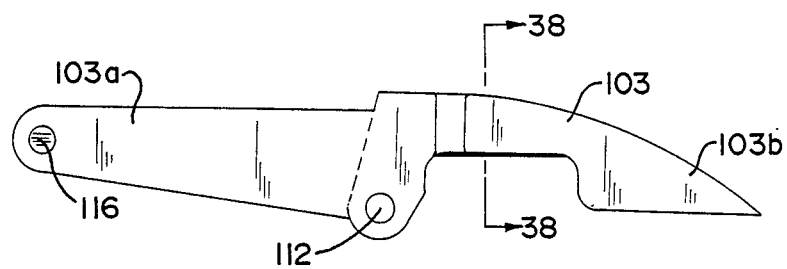
FIG. 35
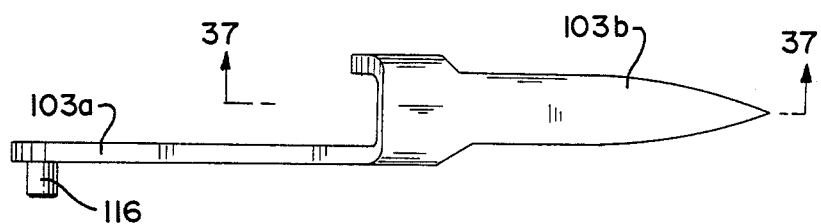
FIG. 36
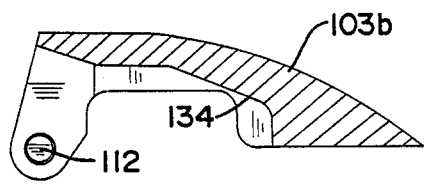 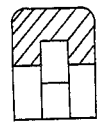
FIG. 37  FIG. 38

APPARATUS FOR EFFECTING OCCLUSION OF THE VAS DEFERENS

The present application is a continuation-in-part application of application Ser. No. 06/884,417 filed on July 11, 1986, now abandoned.

FIELD OF THE INVENTION

The present invention relates to apparatus for occluding subcutaneous target vessels. More particularly, the present invention relates to apparatus for occluding the vas deferens during a vasectomy. Still more particularly, the present invention relates to apparatus for implanting disposable locking clips to effect the percutaneous occlusion of target vessels such as the vas deferens.

BACKGROUND OF THE INVENTION

The procedure which is generally employed in connection with simple vasectomies includes grasping the vas deferens with an appropriate instrument and making an incision to the adjacent subcutaneous tissue. The vasal sheath is then grasped with a clamp and incised with the vas being dissected from the sheath. The vas is then isolated and a segment is excised whereupon the distal end of the vas is electrocoagulated and/or ligated and then buried within the vasal sheath. The proximal end of the vas is also electrocoagulated and/or ligated, and finally the skin can be closed.

Although this procedure has proven to be quite reliable, it is the subject of a number of disadvantages. In particular, this above-described procedure is relatively time-consuming, requiring on the order of at least about 40 minutes or so. The conventional procedure thus requires a surgical incision, entailing all of the necessary precautions normally incident to relatively complicated surgical procedures.

Procedures for the percutaneous occlusion of the vas deferens in a vasectomy have thus been generated in which a mechanical clip is applied to the vas deferens as taught forth in U.S. Pat. No. 4,394,864, in the name of the inventor in the present application. This patent discloses an apparatus and method for effecting occlusion of the vas deferens including a pair of pivotally coupled jaws for receiving a U-shaped locking clip therein, so that after the locking clip is placed between the jaws, closure of the jaws entirely effects closure of the locking clip therein. Although this apparatus has provided a major improvement in the performance of such vasectomies, it relies entirely upon the pivoting of the jaw members to effect the closure of the clip, a movement which is not always desirable in such surgical procedures. The search has therefore continued for improved devices to eliminate this shortcoming and further facilitating the vasectomy procedure.

SUMMARY OF THE INVENTION

In accordance with the present invention, it has now been discovered that the foregoing and other shortcomings can be obviated by applicant's discovery of an apparatus for implanting a disposable locking clip to effect the percutaneous occlusion of a target vessel which includes, first and second jaw members relatively pivotable between open and closed positions and defining a clip retaining cavity therebetween, the clip retaining cavity having sufficient size to accommodate the locking clip therein, clip moving means for slidably moving the locking clip from a retracted position (remote from the clip retaining cavity) to an actuated position (within the clip retaining cavity), and camming means disposed within the clip retaining cavity so that upon slidable movement of the locking clip from the retracted position to the actuated position the camming means causes at least a partial closure of the locking clip.

In accordance with one embodiment of the apparatus of the present invention, the apparatus includes jaw pivot means for pivoting the first and second jaw members between the open and closed positions thereof. In the preferred embodiment the camming means is associated with one of the jaw members, so that upon pivoting of the jaw members into their closed positions, the camming means correspondingly pivots towards the other jaw member further facilitating the partial closure of the locking clip thereby.

In accordance with another embodiment of the apparatus of the present invention, the jaw members include first and second ends, the first ends of the jaw members corresponding to the clip retaining cavity, and the first and second jaw members being relatively pivotable about a fixed pivot point intermediate of the first and second ends of the jaw members, and the jaw pivot means comprising moving means for moving the second ends of the first and second jaw members relative to each other so as to pivot the first and second jaw members about the fixed pivot point to thereby open and close the first ends of the first and second jaw members. In a preferred embodiment the moving means comprises slide means relatively slidable between a first position distal from the clip retaining cavity and a second position relatively close to the clip retaining cavity. In an even more preferred embodiment the slide means includes track means and the second end of one of the first and second jaw members includes track follower means so that upon sliding of the slide means between the first and second positions thereof the track follower means follows the track means thereby moving the second ends of the first and second jaw members relative to each other.

In accordance with another embodiment of the apparatus of the present invention the moving means further comprises handle means for sliding the slide means between the first and second positions thereof. In a preferred embodiment the handle means comprises first and second pivotable handle members, each of which includes a first and a second end and which is pivotable about a fixed pivot point intermediate of the first and second ends thereof, the first ends of the first and second pivotable handle members including gripping means and the second ends of the first and second pivotable handle members being in contact with the slide means. In a highly preferred embodiment the slide means includes slot means substantially transverse to the direction defined by movement of the slide means between the first and second positions thereof, and the second ends of the handle means include first and second slot follower means, so that upon pivoting of the first and second pivotable handle members the first and second slot follower means travel within the slot means while causing the slide means to slide between the first and second positions thereof.

In accordance with another embodiment of the apparatus of the present invention, the clip moving means includes a slidable pusher member including a first end proximate to the clip retaining cavity and a second end distal from the clip retaining cavity. In a preferred embodiment of this apparatus of the present invention the clip moving means includes pivotable handle means including a first end distal from the second end of the slidable pusher member and a second end proximate to the second end of the slidable pusher member and in contact therewith, the pivotable handle means being pivotable about a point intermediate of the first and second ends thereof, so that pivoting of the pivotable handle means results in longitudinal displacement of the slidable pusher member. In a preferred embodiment the slidable pusher member includes groove means substantially transverse to the direction defined by the longitudinal displacement of the slidable pusher member, and the pivotable handle means includes groove follower means. In a preferred embodiment of this apparatus of the present invention, the handle means comprises first and second pivotable handle members, the first pivotable handle member comprising the pivotable handle means, which comprises the clip moving means, and the second pivotable handle member including first and second ends and being pivotable about a fixed pivot point intermediate of the first and second ends thereof, the first ends of the first and second pivotable handle means including gripping means and the second ends of the first and second handle members being capable of contacting the slide means. In a preferred embodiment of this apparatus the slide means includes slot means substantially transverse to the direction defined by movement of the slide means between the first and second positions thereof, and the second ends of the handle means include first and second slot follower means, so that upon pivoting of the first and second pivotable handle members between first and second positions, the first and second slot follower means travel within the slot means while causing the slide means to slide between the first and second positions, and the first slot follower means comprising the groove follower means.

In accordance with one embodiment of this apparatus the slot means includes first and second slot followers associated with the first and second pivotable handle members, the first slot means including an aperture therein so that the first slot follower means can exit the first slot means through the aperture, and the first pivotable handle member being pivotable between a first position at one end of the first slot means and a second position at the other end of the first slot means, the second position being adjacent to the aperture, and the first pivotable handle member being pivotable into a third position in which the first slot following means pivots out of the aperture and remains in the groove means thereby results in longitudinal displacement of the clip moving means.

In accordance with another embodiment of this apparatus one of the first and second jaw members includes an inner surface defining a portion of the clip retaining cavity, and the camming means comprising an angularly displaced wall surface on the inner surface of that jaw member.

In accordance with yet another embodiment of the apparatus of the present invention the apparatus includes switch means slidable between a first position and a second position, the first position locking the slide means in the second position of the slide means relatively close to the clip retaining cavity, and the second position locking the slidable pusher member from longitudinal displacement. In a preferred embodiment of this apparatus of the present invention, the switch means includes hook means for operative engagement with the second end of the pivotable handle member to lock the slide means in the second position of the slide means relatively close to the clip retaining cavity, and tab means for operative engagement with the second end of the pivotable handle means to lock the slidable pusher member from longitudinal displacement.

BRIEF DESCRIPTION OF THE DRAWINGS

A more complete appreciation of the subject matter of the present invention and the various advantages thereof can be realized by reference to the following detailed description, in which reference is made to the accompanying drawings in which:

FIG. 7 is a top, plan, exploded, partial view of the upper and lower jaws of the apparatus shown in FIG. 1 in the entry position;

FIG. 8 is a top, plan, exploded view of the upper and lower jaws of the apparatus shown in FIG. 1 in connection with the vas deferens captured therein;

FIG. 9 is top, plan, enlarged view of the upper and lower jaws of the apparatus shown in FIG. 1 with the jaws open and the locking clip in retracted position therein;

FIG. 10 is a top, plan, enlarged view of the upper and lower jaws of the apparatus shown in FIG. 1 with the locking clip in the advanced position;

FIG. 11 is a top, plan, enlarged view of the upper and lower jaws of the apparatus shown in FIG. 1 with the pusher member in an advanced position initiating closure of the locking clip therein;

FIG. 12 is a top, plan, enlarged view of the upper and lower jaws of the apparatus shown in FIG. 1 with the pusher member in an intermediate forward position and the locking clip further closed thereby;

FIG. 24 is a perspective view of another embodiment of the apparatus in accordance with the present invention;

FIG. 25 is a top, plan, partially sectional view of a portion of the apparatus of FIG. 24;

FIG. 26 is a front, sectional view of the apparatus of FIG. 25, taken along section 26—26 thereof;

FIG. 27 is a top, plan, partially sectional view of the portion of the apparatus shown in FIG. 25, with the clip closed thereby;

FIG. 35 is a top, plan view of the upper jaw of the apparatus shown in FIG. 28;

FIG. 36 is a side, elevational view of the upper jaw shown in FIG. 35;

FIG. 37 is a cross-sectional view of the upper jaw taken on line 37—37 of FIG. 36; and FIG. 38 is a cross-sectional view of the upper jaw taken on line 38—38 of FIG. 35.

DETAILED DESCRIPTION

Figure 1:
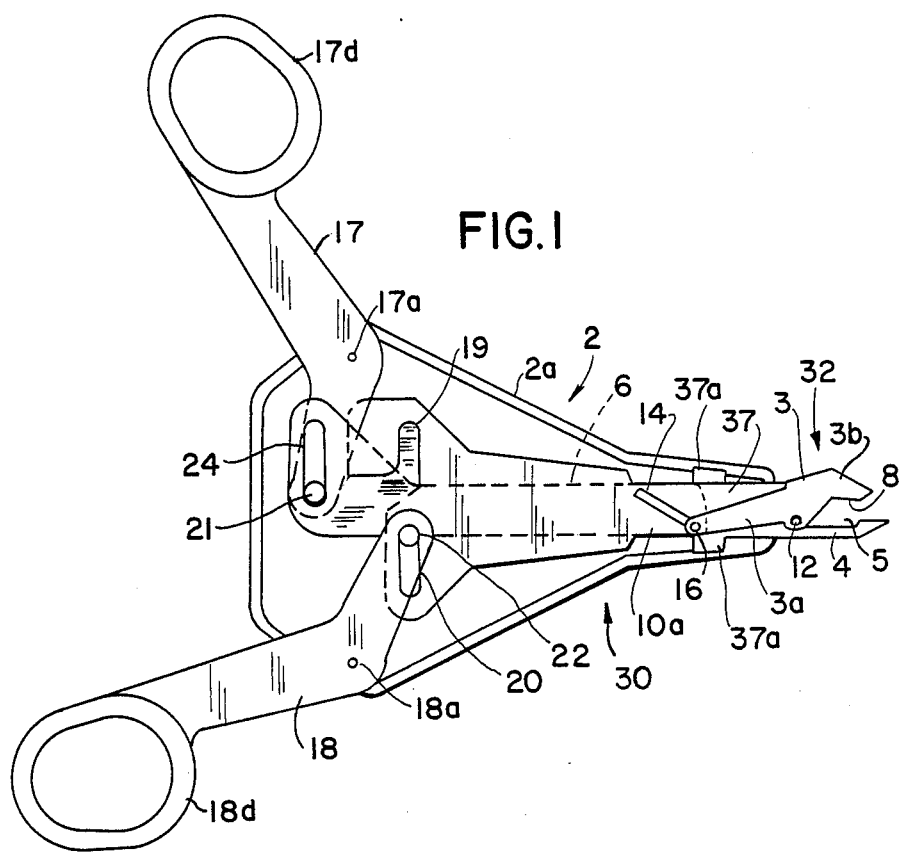
FIG. 1 is a top, plan view of one embodiment of the apparatus in accordance with the present invention, illustrating in particular the inner workings thereof.

The present invention can be more fully appreciated with reference to the accompanying Figures, in which like numerals refer to like portions thereof.

The apparatus of the present invention comprises a compact and highly effective device for implanting closable locking clips in the manner of this invention. The overall apparatus 1 as shown in FIG. 16 includes a body portion 30, a pair of handles 17 and 18, and a front end 32 comprising a pair of jaws 3 and 4 terminating in a trocar-type obturator configuration 7.

Figure 16:
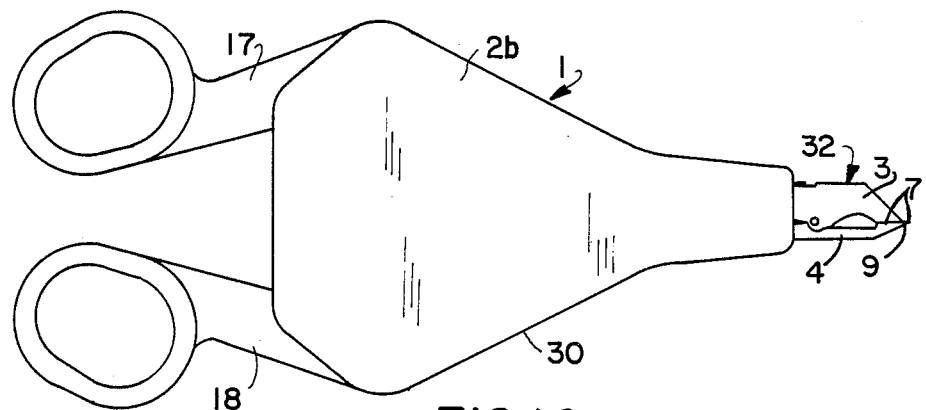
FIG. 16 is a top plan view of the apparatus shown in FIG. 1, wherein the housing cover is in assembled position.
Figure 17:
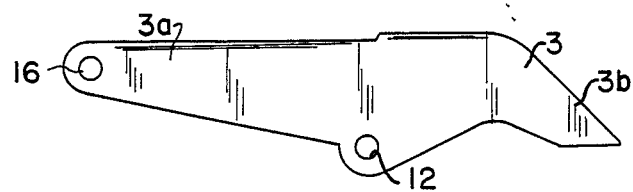
FIG. 17 is a top, plan view of the upper jaw of the apparatus shown in FIG. 1.
Figure 18:
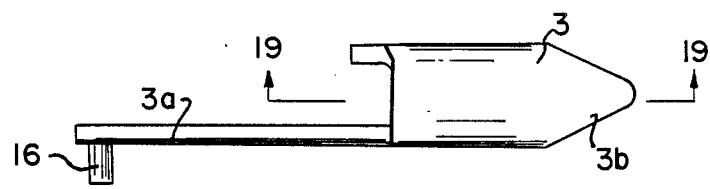
FIG. 18 is a side, elevational view of the upper jaw shown in FIG. 17.
Figure 19:
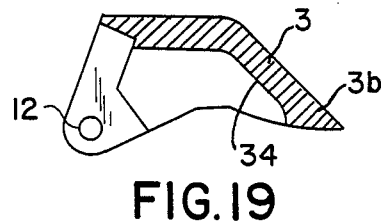
FIG. 19 is a cross-sectional view of the upper jaw taken on line 19—19 of FIG. 18.
Figure 22:
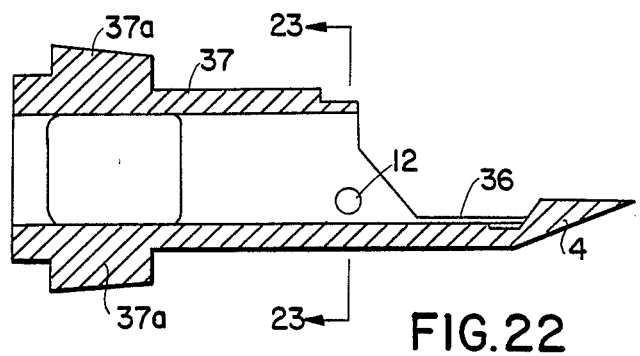
FIG. 22 is a side, cross-sectional view of the lower jaw taken on line 22—22 of FIG. 21.
Figure 23:
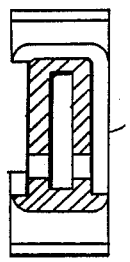
FIG. 23 is a cross-sectional view of the lower jaw taken on line 23—23 of FIG. 22.
Figure 21:
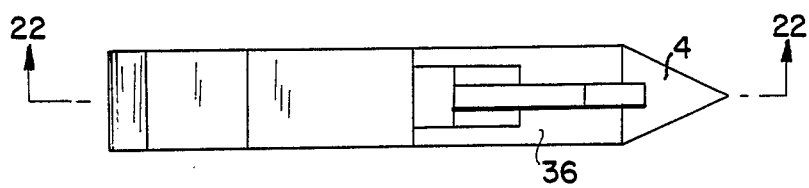
FIG. 21 is a side, elevational view of the lower jaw shown in FIG. 20.
Figure 20:
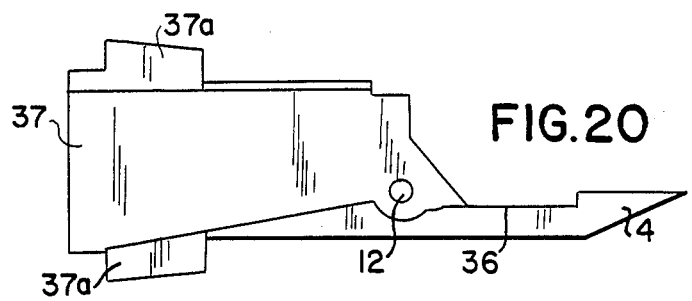
FIG. 20 is a top, plan view of the lower jaw of the apparatus shown in FIG. 1.

The body portion 30 includes two housing portions 2a and 2b as can be seen in FIGS. 1 and 16 hereof. These two housing halves 2a and 2b can be welded together around the periphery to form housing 2, which includes appropriate openings for the handle members 17 and 18 and the front end 32. The trocar obturator 7 facilitates a variety of functions including penetrating and cutting through tissue, trapping a target vessel, and holding and implanting a clip on a target vessel.

The penetration function thereof is accomplished when the trocar obturator is moved in a forward direction. It is adapted for penetration of tissue by the provision of a barb-shaped end 9 as shown in the Figures. Forward movement of the trocar obturator 7 thus brings the barb-shaped end 9 into contact with the tissue. The pressure resulting from forward movement of the trocar obturator 7 thus effects penetration by pushing the barb-shaped end 9 into the tissue. The remaining functions of the trocar obturator 7 will be more fully appreciated following a detailed description of the trocar obturator 7.

Thus, turning to FIG. 1, the front end 32 of the device of the present invention includes a pair of jaw members 3 and 4 which are pivotably connected at pivot point 12. Upper jaw member 3 and lower jaw member 4 are illustrated in detail in FIGS. 17-19 and FIGS. 20-23, respectively. As shown in FIGS. 9-13 and 17-19, the upper jaw 3 is cup-shaped in form. Thus, the inner surface of the upper jaw 3 includes an inner wall surface comprising a forward camming surface 34 therewithin. As shown in FIGS. 9-13 and 20-23, the lower jaw 4 includes a substantially flat or planar upper surface 36, and therefore upper jaw 3 and lower jaw 4 define a clip retaining cavity 5 therebetween.

Referring specifically to FIGS. 17-23, the configuration of upper jaw 3 and lower jaw 4 and thus the manner in which these jaw members are operatively associated, can be seen. Thus, the rear portion of jaw 3 is telescopically inserted into the passage of jaw 4 (shown in FIG. 23) so that camming surface 34 of jaw 3 is positioned above planar upper surface 36. The jaw members are then connected at pivot point 12.

The lower jaw 4 is intended to remain substantially fixed in the position shown in FIG. 1 so that upon pivoting of the upper jaw 3 about pivot point 12 the jaw can open and close, thus opening and closing the clip retaining cavity 5. In order to maintain the lower jaw 4 in a relatively fixed position the jaw includes a rearwardly extending portion 37 having outwardly extending tabs 37a on either side. These tabs act to fix the lower jaw with respect to the housing portion 2b.

Figure 3:
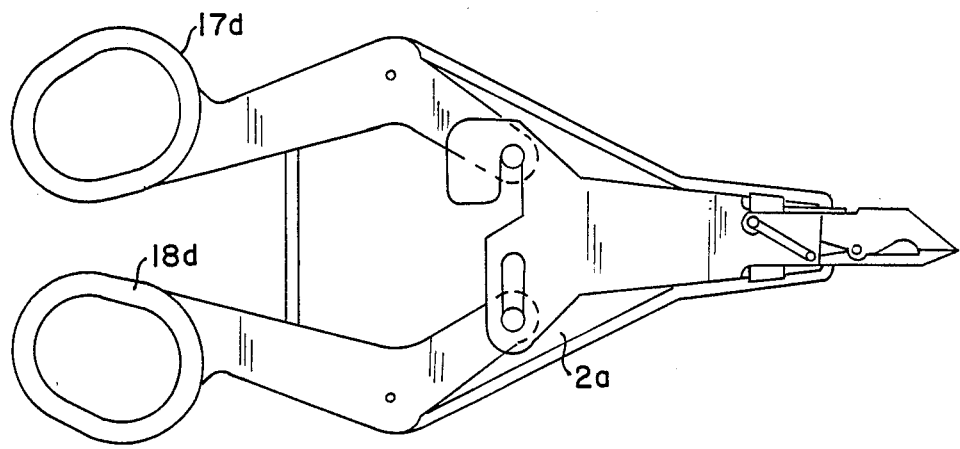
FIG. 3 is a top, plan view of the apparatus shown in FIG. 1, wherein the handle members and the jaw members are shown in the closed position.

Since the upper jaw 3 is pivoted to the lower jaw 4 at pivot point 12, closing of the forward portion of upper jaw 3 is effected by lifting the rear portion 3a thereof. This, in turn, is accomplished by utilization of the moving means or slide 10 which is slidably disposed within the housing 2. Thus, the moving means 10 can slide from a distal position as shown in FIG. 1 remote from the clip retaining cavity, and a proximate position as shown in FIG. 3 adjacent to the clip retaining cavity. The forward end 10a of the moving means 10 adjacent to the jaw members 3 and 4 includes an angularly disposed track 14 extending therethrough. In addition, a track follower 16 extends from the rear portion 3a of the upper jaw 3 into the track 14. Therefore upon sliding motion of the moving means 10 from the position in FIG. to that in FIG. 3, the track follower 16 follows track 14 to raise the rear portion 3a of the upper jaw 3 which pivots about pivot point 12 to close the forward end 3b of the upper jaw 3 towards the fixed lower jaw 4. Thus, when the moving means 10 is in the forward position shown in FIG. 3 the jaws 3 and 4 are in a fully closed position.

The above-described linear reciprocation of the moving means 10 within the housing 2 is effected by the action of handles 17 and 18. More particularly, the rearward end of moving means 10 includes a pair of transverse slots 19 and 20, both of which are shown in FIGS. 1-4. The lower slot 20 is located in an enlarged end portion 10b of the slide 10, while the upper slot 19 is located in an enlarged portion 10c of the slide 10. However, the upper slot 19 is not fully enclosed, and includes an aperture 38 extending rearwardly therefrom. The aperture is thus defined by end portion 10c of the slide 10 and an extending tab portion 10d thereof.

Figure 4:
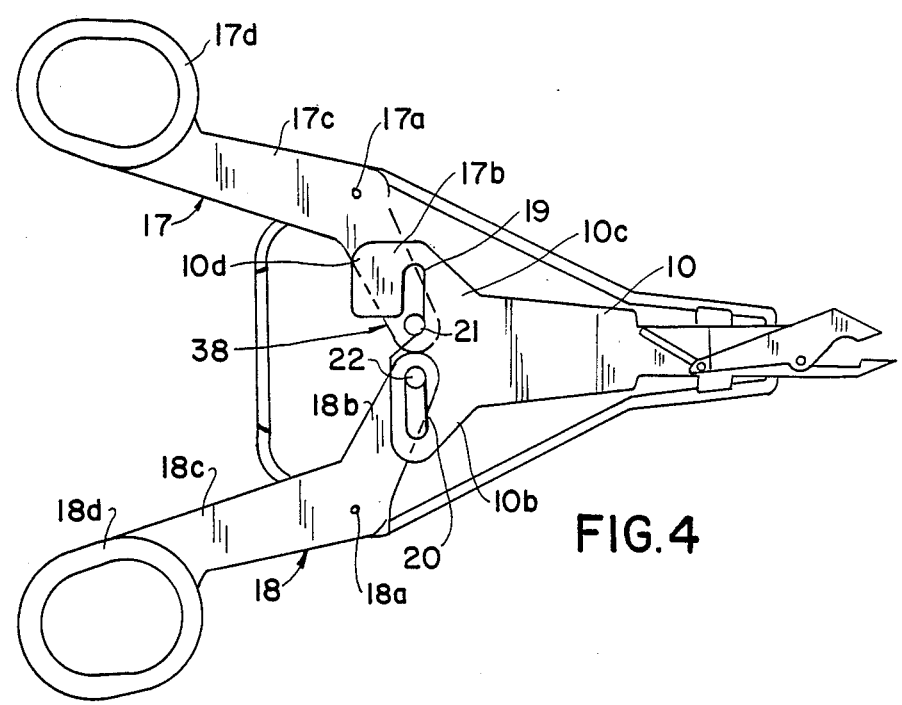
FIG. 4 is a top, plan view of the apparatus shown in FIG. 1, wherein the jaw members are shown in the open position, and handle 17 is shown in a partially closed position.

Turning to handles 17 and 18, handle 17 is pivoted about a pivot point 17a where handle 17 is pivotally connected to housing portion 2b. Handle 17 includes a forward depending leg portion 17b angularly disposed with respect to rearward leg portion 17c which terminates in grip or finger hole 17d. Thus, rotation of the grip 17d about pivot point 17a causes corresponding displacement of the forward portion 17b of the handle 17. Disposed at the forward portion 17b of the handle 17 is a projecting slot follower 21 extending into slot 19. In this manner, rotation of the handle 17 in a downward direction as shown in FIG. 4 causes the slot follower 21 to move upwardly into the position shown in FIG. 3. However, because the slot follower 21 is located below pivot point 17a, the motion of the slot follower 21 is not exclusively transverse with respect to the longitudinal direction of slide 10, but includes a forward longitudinal component directed towards the jaws 3 and 4. This, in turn, causes the slide 10 to move forwardly into the position shown in FIG. 3, at which position the slot follower 21 reaches the upper end of slot 19.

Handle member 18 operates in a like manner. Thus, pivoting of the rearward leg portion 18c of the handle 18 by means of grip or finger hole 18d about pivot point 18a causes the corresponding pivoting of the forward depending leg portion 18b and its corresponding slot follower 22 extending therefrom, which can then move within slot 20 in the same manner as discussed above with respect to follower 21 and slot 19. Thus, as slot follower 22 is located above pivot point 18a, pivoting of handle member 18 in an upward direction from the position shown in FIGS. 1 or 4 to that shown in FIG. 3 also includes a forward component to urge the slide member 10 forwardly towards the jaw members 3 and 4, again facilitating the closure of the jaws in the manner discussed above.

Figure 2:
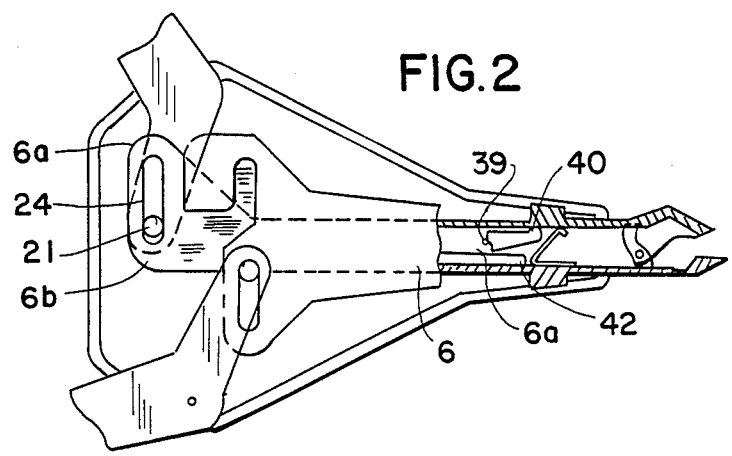
FIG. 2 is a top, plan, partial view of a portion of the apparatus shown in FIG. 1, showing the front end thereof in partial cross-section.
Figure 5:
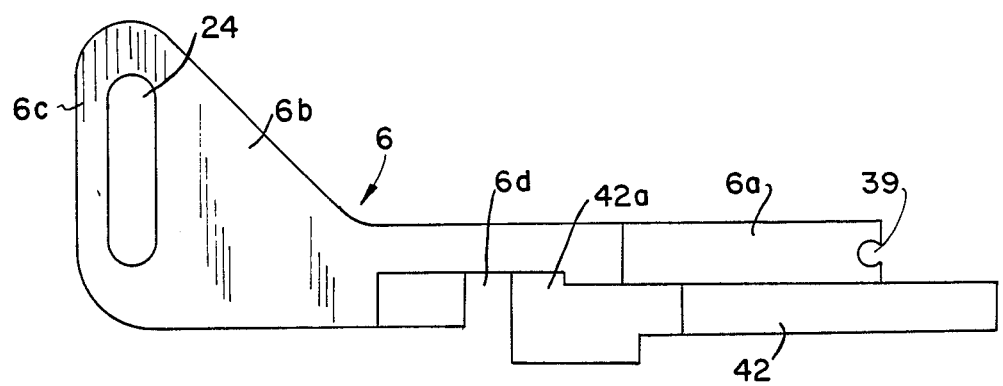
FIG. 5 is a top, plan view of the clip moving component of the apparatus shown in FIG. 1.
Figure 6:
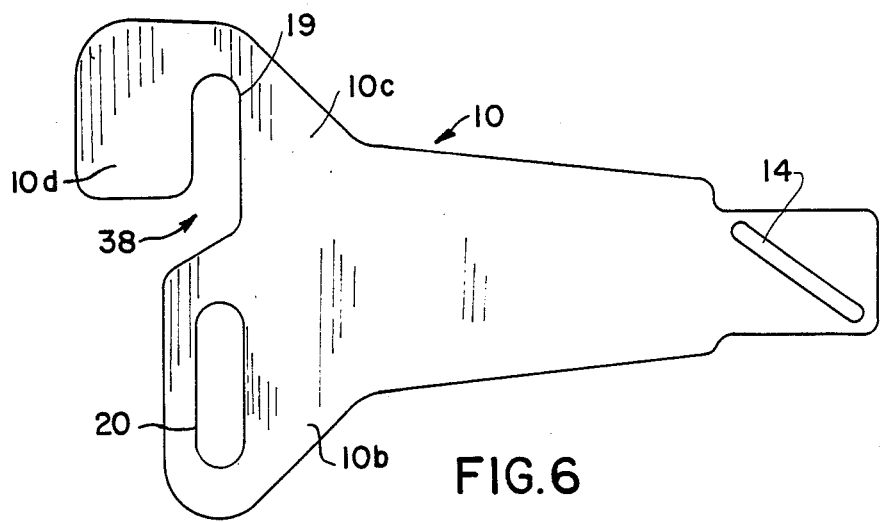
FIG. 6 is a top, plan view of the upper jaw actuating component of the apparatus shown in FIG. 1.

Longitudinally and slidably contained within the housing 2 is clip moving means 6, which is shown apart from the apparatus of the present invention in FIG. 5 and operatively assembled therewith in FIGS. 1 and 2. This elongated element 6 includes a forward end 6a which preferably includes an aperture 39 with a reduced opening into which can be fit the corresponding enlarged circular extension 40a of a pusher member 40 so that the pusher member 40 extends therefrom in the manner shown in FIGS. 2 and 9-13. In addition, a secondary pusher member 42 is slidably juxtaposed below clip moving means 6 by means of shoulder 42a being disposed in recess 6d so that its forward end extends forwardly in the manner shown in FIGS. 2 and 5, where it is below pusher member 40. The rearward end 6b of the clip moving means 6 includes an upstanding leg portion 6c which includes a transverse groove 24 extending therethrough. The clip moving means 6 is slidable between the retracted position shown in FIG. 2 and a forward position in which the groove 24 is in alignment with transverse slot 19 of slide 10. When the clip moving means 6 is in this position the pusher member 40 extends into the clip retaining cavity 5 in a manner discussed below in particular detail with respect to FIGS. 9-13.

Upon opening movement of handle 17 it can be seen that the slide follower 21 extending from the leg portion 17b of handle member 17 can continue to rotate in a clockwise direction in the configuration shown in FIG. 4 and thus exit the transverse slot 19 through aperture 38. Since the slide follower 21 is still projecting into the groove 24 of clip moving means 6, its continued clockwise motion from the position in FIG. 4 to that in FIG. 1 causes the slide member 10 to slide longitudinally from the advanced position thereof to the retracted position, which can be clearly seen in FIG. 2. Thus, the same handle member 17 can be used to manipulate both the slide member 10 and clip moving means 6 depending upon the degree of rotation thereof about pivot point 17a. The capability to control both the movement of the clip moving means 6 with respect to the clip retaining cavity 5, and the opening and closing of jaw members 3 and 4, by the use of handle members 17 and 18 provides a simple and efficient method by which the overall function of the present apparatus can be easily accomplished by a surgeon.

Referring now to FIGS. 7-13, the actual procedure for implanting locking clips to effect percutaneous occlusion of the vas deferens utilizing the embodiment of the present invention as shown in FIGS. 1-6 and 14-16 will now be described.

Figure 13:
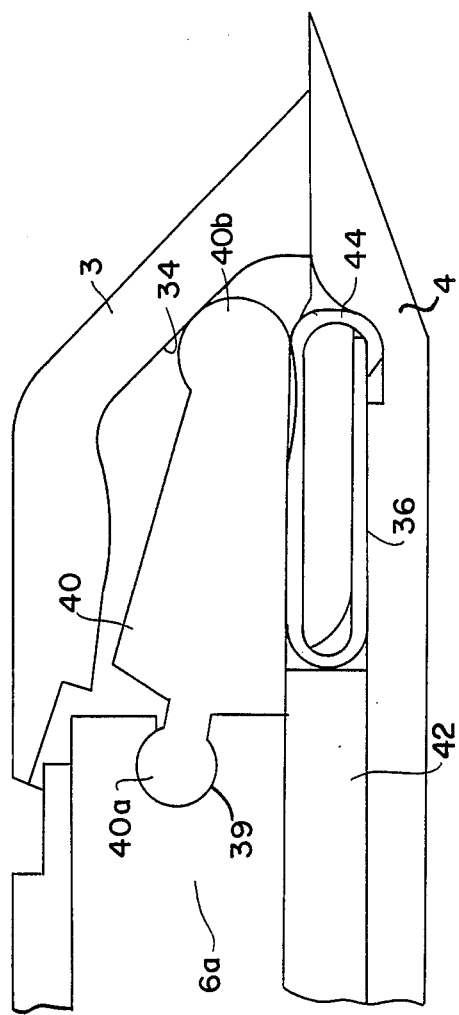
FIG. 13 is a top, plan, enlarged view of the upper and lower jaws of the apparatus shown in FIG. 1 with the jaws closed and the locking clip closed therein.
Figure 14:
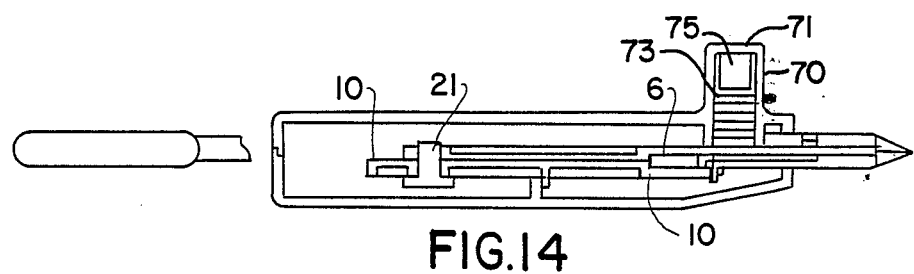
FIG. 14 is a side, elevational, partial view of the apparatus shown in FIG. 1, illustrating in particular the positioning and configuration of the respective sliding members and the clip delivering cartridge.
Figure 15:
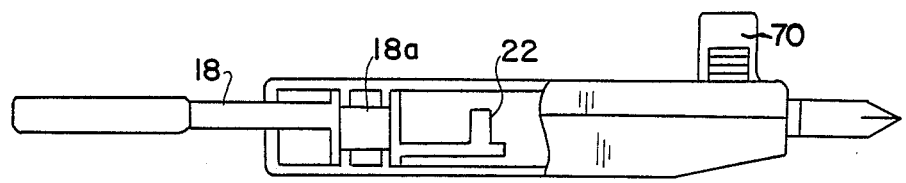
FIG. 15 is a side, elevational, partial view of the apparatus in FIG. 1, illustrating in particular the arrangement of handle 18.

In the entry position shown in FIG. 7, in which the handle members 17 and 18 are in the configuration shown in FIG. 3, the device is introduced by piercing the skin, again by simply moving the device forward while grasping the handles 17 and 18. It should also be appreciated that at this point there is no clip within the clip retaining cavity 5. The clip itself, a sample of which can be seen in FIGS. 9-13 where it is generally designated as 44, is maintained in cartridge 70 which holds a number of clips in alignment therein, as shown in FIGS. 14 and 15.

Cartridge 70, extending outwardly from housing portion 2a, has a spring 75 which exerts a force between end caps 71 and clip pusher 73, thereby constantly urging the clips 44 toward clip moving means 6. When the clip moving means 6 is moved to the retracted position shown in FIG. 2, the proximate clip 44 in cartridge 70 will advance transversely into position in front of pusher 40 and secondary pusher 42 of slide 6, whereby the clip 44 can be moved in a forward direction toward the clip retaining cavity 5 by the rotation of handle member 17, as discussed further below. The remainder of the clips in cartridge 70 are similarly urged transversely so as to be in position for subsequent clamping operations.

As the device is moved further, the trocar obturator configuration 7, with barb 9, continues to move forward towards the vas deferens of the urogenital system. As the vas deferens is approached, the surgeon begins to pivot the upper jaw 3 into an open position by spreading the handle members 17 and 18 from the position shown in FIG. 3 to that shown in FIG. 4. Again, this causes the forward ends 17b and 18b to rotate towards each other, thereby causing the extending slot followers 21 and 22 to rotate within their respective slots 19 and 20, thereby urging the slide member 10 away from the clip retaining cavity 5. This action simultaneously causes the inner end 3a of the upper jaw 3 to rotate downwardly or in a counterclockwise direction as the slot follower 16 thereof travels downwardly in slot 14, thereby opening the jaw into the position shown in FIG. 4.

The surgeon then locates the vas deferens 60 between the jaws in the manner shown in FIG. 8 immediately after piercing the surrounding tissue to expose the same. The surgeon can now remove the device slightly in a rearward direction to again expose the vas deferens 60. With the jaws in the open position, and the clip 44 in its retracted position, the surgeon can now proceed to move the clip into its position within the clip retaining cavity 5, as shown in FIGS. 9 and 10. This is easily accomplished by first retracting the clip moving means 6 (by continuing to rotate handle member 17 in a clockwise direction into the position shown in FIG. 1) whereby the clip 44, in its retracted position will have moved from clip cartridge 70 into the position shown in FIG. 2. By next rotating the handle member 17 in a counterclockwise direction, whereby the slot follower 21 within slot 24 similarly moves in a clockwise direction to urge the clip moving means 6 in a forward direction towards the clip retaining cavity 5, the pusher member 40 in conjunction with the secondary pusher 42 moves the clip 44 towards the clip retaining cavity 5, again as shown in FIG. 9. Because of the location and configuration of pusher member 40 at the upper end of the clip 44, pressure is maintained on the upper end of the clip as it moves forward. In any event, continued motion of the handle member 17 in a counterclockwise direction as discussed above continues to urge the clip towards the clip retaining cavity 5 until it reaches the same as shown in FIG. 10.

At this point, the vas deferens 60 is contained within cavity 5 and clip 44. Thus, continued motion of the clip moving means 6 in the forward direction will cause the clip 44 to begin closing as shown in FIGS. 11-13, initially by means of the pusher member 40 and secondary pusher member 42 so as to urge the upper end of the clip 44 against the camming surface 34. As the clip moving means 6 continues to move forward, the clip 44 begins to close against the camming surface 34, as is particularly illustrated in FIGS. 11 and 12. At the same time, further closure and final closing of the clip 44 into the configuration shown in FIG. 13 is ultimately caused by a combination of continued movement of the pusher member 40, whereby its boss member 40b bears against the camming surface 34 and additional closure of the jaw members 3 and 4, such continued movement being facilitated by pivoting of handle members 17 and 18 into the closed configuration shown in FIG. 3. More specifically, after rotation in a counterclockwise direction of handle 17 is completed to the extent that the slot follower 21 enters the slot 19, continued closure of the handle members 17 and 18, i.e., so that the handle members approach each other, now closes the jaw members 3 and 4, thus resulting in complete closure of the clip around the vas deferens as shown in FIG. 13. It should be noted that the closing and locking of clip 44 is further facilitated by means of recess 4a and camming surface 4b of jaw member 4, both of which features are shown in FIGS. 9-13. As the foot 44a at the upper end of clip 44 is urged toward jaw member 4, surface 44b at the tip thereof will first bear against camming surface 4b. Further movements of clip 44 by means of pusher member 40 will cause the foot 44a of clip 44 to turn inwardly as surface 44b bears against surface 4b. Continued movement of pusher member 40 will urge foot 44a into recess 4a where the same will be folded about end 44c of clip 44, thereby locking the clip 44 around the vas deferens.

The occlusion of the vas deferens is now complete, preventing the passage of sperm from the testes to the ejaculatory duct. Removal of the device from the vas deferens 60 is now accomplished by opening the jaw members 3 and 4 and merely removing the device therefrom.

Thus, the present invention accomplishes occlusion of the vas deferens in a rapid and efficient manner. Typically under about 5 minutes, with minimum invasion of the body, is required.

DETAILED DESCRIPTION OF A PREFERRED EMBODIMENT

Figure 28:
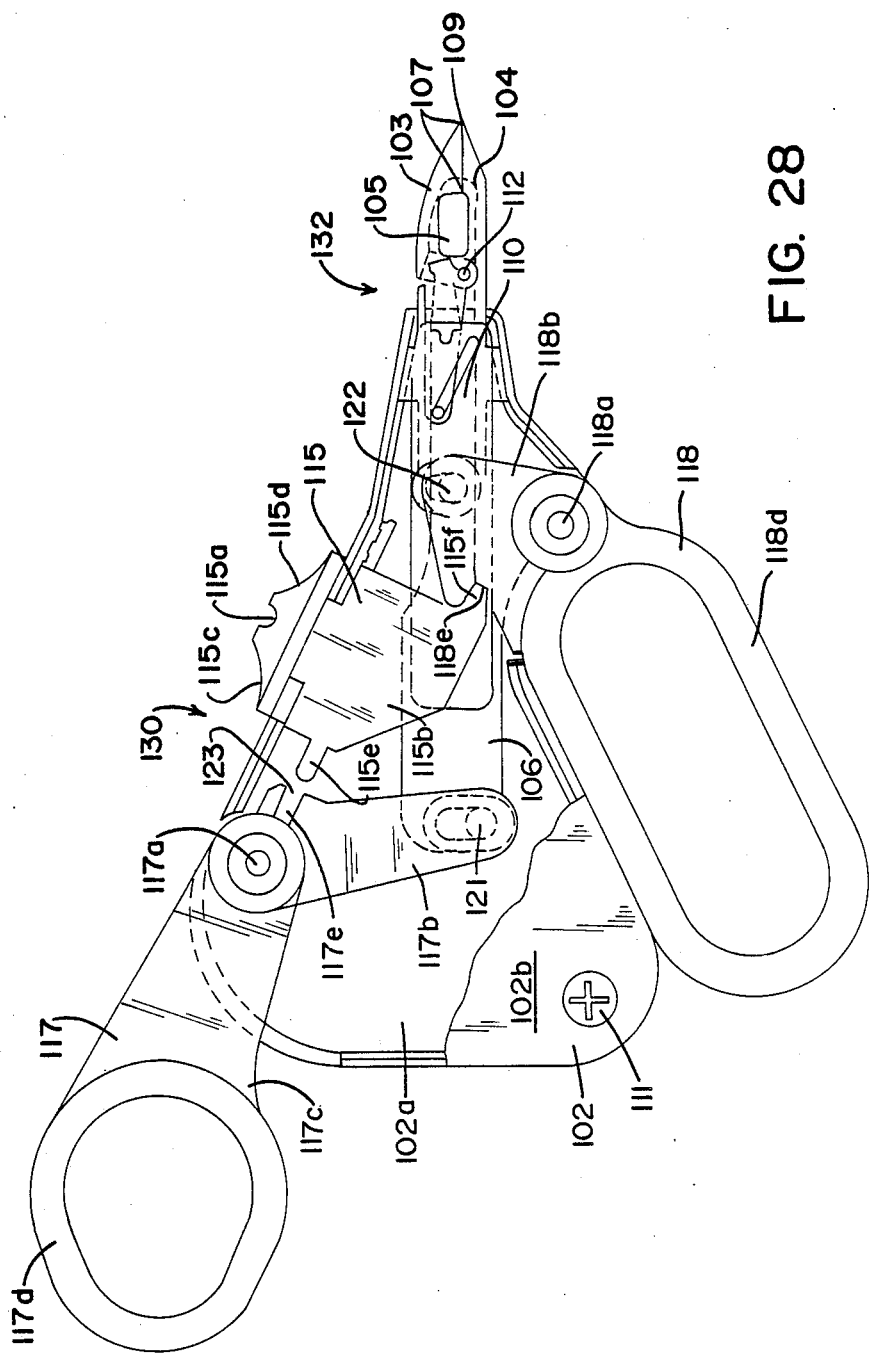
FIG. 28 is a top, plan view of a preferred embodiment of the apparatus in accordance with the present invention, with the top cover partially broken away to illustrate in, particular the inner workings thereof, and showing the selector switch in position to advance and close a locking clip about the vas deferens.
Figure 29:
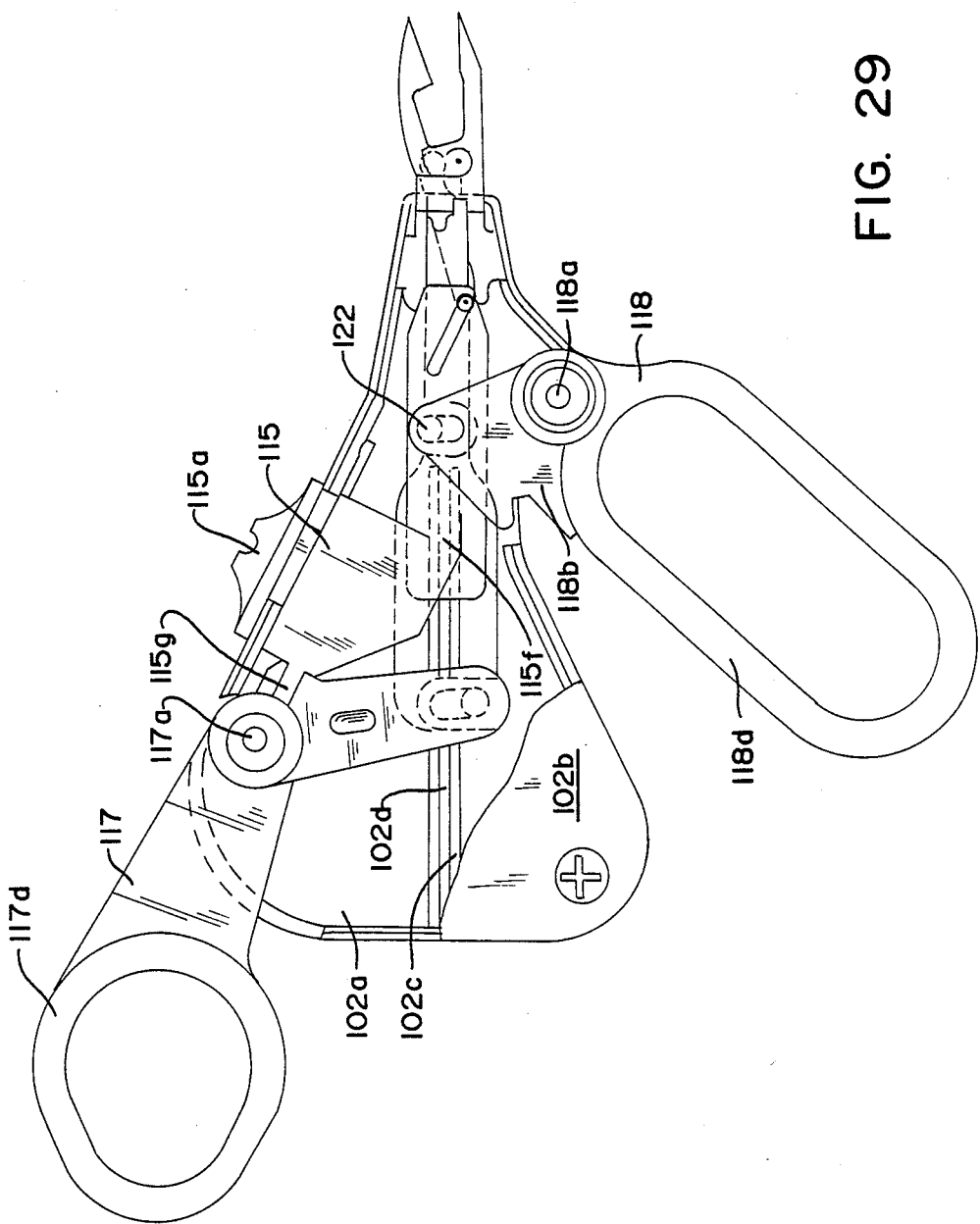
FIG. 29 is a top, plan view of the apparatus shown in FIG. 28, showing the selector switch in position for opening or closing the jaw members.

A highly preferred embodiment of the apparatus of the present invention is shown in FIGS. 28-38. As can be seen in FIG. 28, the overall apparatus 100 includes a body portion 130, a pair of handles 117 and 118, a selector switch 115, and a front end 132 comprising a pair of jaws 103 and 104 terminating in a trocar obturator configuration 107.

The body portion 130 includes two housing members 102a and 102b which can be assembled by threaded means, as at 111, or any other suitable means. In assembled position, housing members 102a and 102b include openings for the handle members 117 and 118, the front end 132 and the selector switch 115. The trocar obturator 107 operates in the same manner as the trocar obturator 7 of the previously described embodiments. Thus, sharply pointed end 109 penetrates and cuts through tissue so that trocar obtruator 107 may trap a target vessel and implant a clip thereon.

As can be seen in FIG. 28, the jaw members 103 and 104 of the preferred embodiment of the present invention are pivotably connected at pivot point 112. Upper jaw member 103, shown in detail in FIGS. 35-38, is cup-shaped in form, and includes an inner wall surface comprising a forward camming surface 134. The lower jaw 104, shown in detail in FIGS. 32-34, includes a substantially flat upper surface 136. Upper jaw 103 and lower jaw 104 thus define a clip retaining cavity 105 therebetween.

Jaw members 103 and 104 are associated and operated in a manner substantially similar to that described above with regard to the apparatus of FIG. 1. Thus, lower jaw 104 includes a rearwardly extending portion 137 having outwardly extending tabs 137a on either side which act to substantially fix the position of the lower jaw with respect to the housing portion 102b. By utilizing slide 110, slidably disposed within the housing 102, to pivot the upper jaw 103 about pivot point 112, the jaws can be opened and closed. The forward end 110a of the slide 110 adjacent to the jaw members 103 and 104 includes an angularly disposed track 114 extending therethrough. A track follower 116, extending from the rear portion 103a of the upper jaw 103 into the track 114, follows track 114 as slide 110 is moved from a distal position remote from the clip retaining cavity 105 to a proximate position adjacent to the clip retaining cavity 105, and thereby raises rear portion 103a of the upper jaw 103 so that the forward end 103b of the upper jaw 103 closes toward the fixed lower jaw 104. Thus, when the slide 110 is in the proximate position shown in FIG. 28 the jaws 103 and 104 are in a fully closed position.

Figure 31:
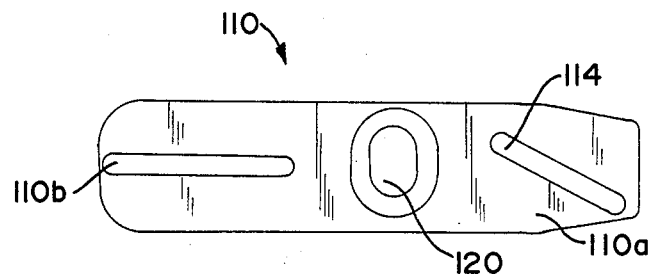
FIG. 31 is a top, plan view of the upper jaw actuating component of the apparatus shown in FIG. 28.
Figure 32:
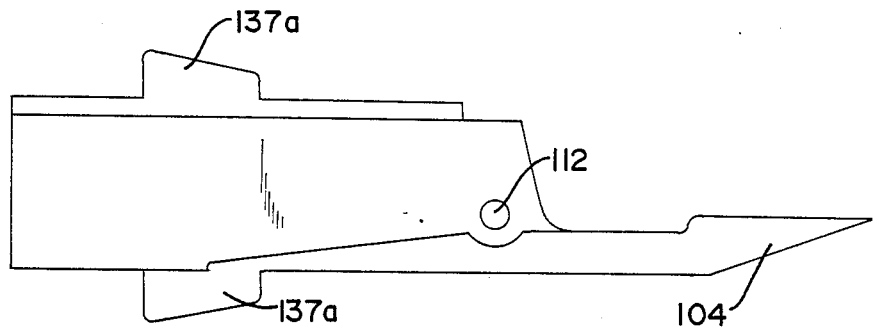
FIG. 32 is a top, plan view of the lower jaw of the apparatus shown in FIG. 28.
Figure 33:
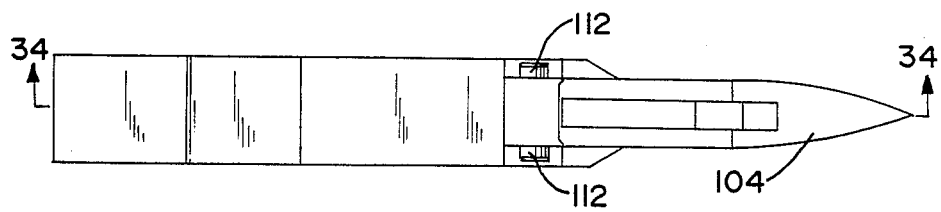
FIG. 33 is a side, elevational view of the lower jaw shown in FIG. 32.
Figure 34:
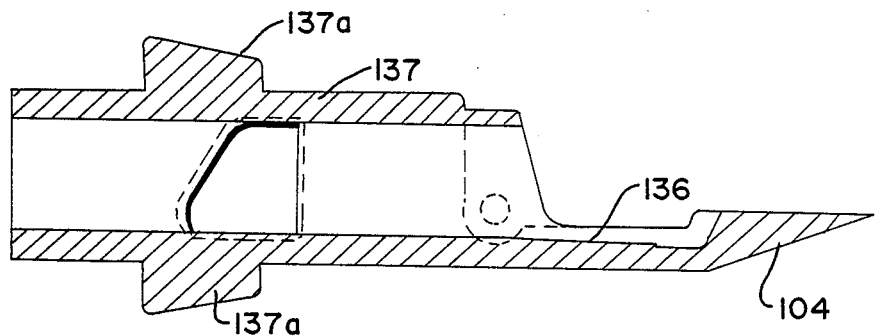
FIG. 34 is a cross-sectional view of the lower jaw taken on line 34—34 of FIG. 33.

The movement of slide 110 within the housing 102 is effectuated by the action of handle 118. As shown in FIG. 31, the central portion of slide 110 includes transverse slot 120. Handle 118, pivotally connected between housing members 102a and 102b at pivot point 118a, includes a forward portion 118b and a rearwardly projecting grip or finger hole 118d. Rotation of the grip 118d about pivot point 118a will thus result in a corresponding displacement of the forward portion 118b of the handle 118. Disposed at the forward portion 118b of the handle 118 is a projecting slot follower 122 extending into the slot 120 of the slide 110. Since the slow follower 122 is located above the pivot point 118a, the motion of the slot follower 122 includes a forward longitudinal component directed toward the jaws 103 and 104. This, in turn, causes the slide 110 to move forwardly into the position shown in FIG. 28, at which position the slot follower 122 reaches the lower end of the slot 120.

Figure 30:
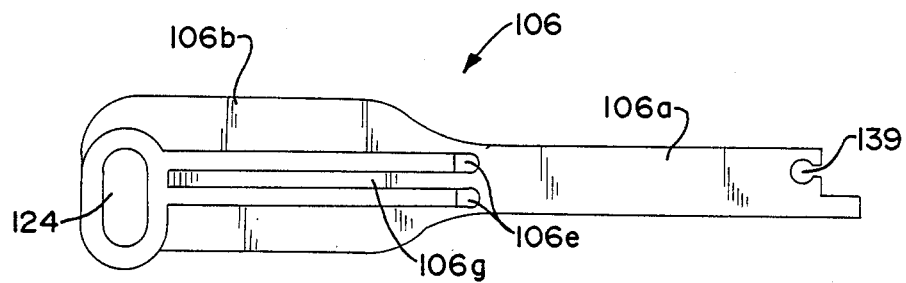
FIG. 30 is a top, plan view of the clip moving component of the apparatus shown in FIG. 28.

Longitudinally and slidably contained within the housing 102 is clip moving means 106, shown separately in FIG. 30. A forward end 106a of clip moving means 106 includes an aperature 139 with a reduced opening, sized and shaped for mating engagement with the enlarged circular extension 140a of a pusher member 140 in the manner described in the previous embodiment and as shown in FIGS. 9–13 thereof. The rearward end 106b of the clip moving means 106 includes a transverse groove 124 extending therethrough. The clip moving means 106 is slidable between a retracted position remote from the clip retaining cavity 105 and a forward position proximate to the clip retaining cavity 105. When the clip moving means 106 is in the forward position the pusher member 140 extends into the clip retaining cavity 105 in a manner discussed more particularly below.

Longitudinally disposed ribs on the slide 110 and the clip moving means 106 keep these members properly aligned and spaced with respect to one another and to the housing 102. Thus, ribs 110b and 110c are longitudinally disposed on either side of the slide 110, and ribs 106e and 106f are longitudinally disposed on either side of the clip moving means 106, ribs 106e defining channel 106g therebetween. In assembled position, rib 110b engages housing member 102a and rib 110c matingly engages and is guided by channel 106g. Rib 106f, in turn, matingly engages and is guided by channel 102d formed between longitudinally disposed ribs 102c on housing member 102a. This association enables the reciprocating movement of the slide 110 and the clip moving means 106 within the housing 102 so that the apparatus of the present invention may properly function without jamming or binding.

The movement of the clip movement means 106 between the forward position and the retracted position is effected by the action of handle 117. Handle 117, pivotally connected between housing portions 102a and 102b about pivot point 117a, includes a forward depending leg portion 117b angularly disposed with respect to rearward leg portion 117c which terminates in grip or finger hole 117d. Disposed at the forward portion 117b of the handle 117 is a projecting slot follower 121 extending into slot 124. Thus, rotation of the handle 117 in a counterclockwise direction causes a corresponding displacement of the forward portion 117b thereof, so that the slot follower 121 moves upwardly within slot 124. However, since the slot follower 121 is located below pivot point 117a, the motion of the slot follower 121 includes a forward longitudinal component directed towards the jaws 103 and 104, which causes the clip moving means 106 to move forwardly into the clip retaining cavity 105.

Slidably mounted between housing members 102a and 102b is a selector switch 115. Top portion 115a of selector switch 115 extends outwardly from an opening formed in the side of the housing and includes oppositely disposed curved surfaces 115c and 115d for forward and rearward activation of the switch 115. The bottom portion 115b of the switch 115 includes a forwardly extending hook 115f which, when the selector switch is in forward position, matingly engages a recess 118e formed in the forward portion 118b of handle 118. The hook 115f can only mate with the recess 118e when the handle 118, and thus the jaw, is in a fully closed position. Thus, jaw members 103 and 104 can be locked in the closed position by the movement of selector switch 115 into the forward position.

Projecting rearwardly from the bottom portion 115b of selector switch 115 is a tab member 115e which, when the selector switch 115 is in a rearward position, matingly engages slot 117e formed on the lower portion 117b of handle 117 adjacent to pivot point 117a. Slot 117e, however, is not fully enclosed, and includes an aperture 123 extending forwardly therefrom. By sliding selector switch 115 in a rearward direction, tab 115e can enter aperture 123 and mate with slot 117e. Handle 117 can only be locked in place by this action when in the fully closed position, with clip moving means 106 extended fully forward into clip retaining cavity 105. The rearward positioning of selector switch 115 removes the hook 115f from the recess 118e in the forward portion 118b of the handle 118 so that the jaw members 103 and 104 may be opened. Similarly, the forward positioning of the selector switch 115 removes the tab 115e from the slot 117e in the bottom portion 117b of the handle 117 so that the clip moving means 106 may be retracted from or advanced toward the clip retaining cavity 105. Thus, as only one of handles 117 and 118 can be operated at a time, the preferred embodiment is simpler and less awkward to use than the embodiment previously described above.

As the preferred embodiment of the present invention operates in a manner substantially similar to the embodiment previously described, reference can be made to FIGS. 7–13 thereof in describing the actual procedure for implanting locking clips to effect percutaneous occlusion of vas deferens. That is, although there are differences in operation of these overall devices, the resultant action of the respective front ends 32 and 132 thereof are substantially identical.

In the entry position shown in FIG. 7, the handles 117 and 118 are in the closed configuration and the selector switch 115 is in the forward position, thereby locking jaws 103 and 104 closed, all of which can readily be seen in FIG. 28. Additionally, there is no clip present within the clip retaining cavity 105. The clip, generally designated as 44, is the same as that used in the previous embodiment discussed above. Cartridge 70, similar to that shown in FIG. 14 and 15, maintains a number of clips in alignment therein, feeding them one at a time to the clip moving means 106 as discussed above.

As the device is moved forward, the pointed tip 109 of the trocar obturator configuration 107 pierces the skin and moves toward the vas deferens of the urogenital system. As the vas deferens is approached, the surgeon slides selector switch 115 rearwardly so that handle 118 can be downwardly rotated. This causes the forward end 118b to rotate in a counterclockwise direction which urges the slide 110 away from jaws 103 and 104. Inner end 103a of the upper jaw 103 is simultaneously rotated downwardly or in a counterclockwise direction as the slot follower 116 thereof travels downwardly in slot 114, thereby opening the jaw to the position shown in FIG. 29.

As shown in FIG. 8, the surgeon pierces the surrounding tissue to expose the vas deferens 60 and locates the same between the jaws 103 and 104. Once the vas deferens 60 is so located, handle 118 is rotated in a clockwise direction which urges slide 110 forwardly. This, in turn, causes the inner end 103a of the upper jaw 103 to rotate upwardly or in a clockwise direction as the slot follower 16 thereof travels upwardly in slot 114, thereby closing jaw members 103 and 104 into the position shown in FIG. 28. When the jaws 103 and 104 have obtained a fully closed position, they can be locked therein by moving selector switch 115 to a forward position, thereby engaging hook 115f in recess 118e as previously described. Since hook 115f will only become aligned with recess 118e when the jaws 103 and 104 are fully closed, the ability or inability to slide the selector switch to the forward position serves to indicate to the surgeon the position of jaw members 103 and 104 with respect to one another.

At this point, with the selector switch 115 in a forward positon, handle 117 may be freely rotated to move the clip 44 into its position within the clip retaining cavity 105, as can be understood by reference to FIGS. 9–13. It should be emphasized at this point that the reference to FIGS. 9–13 in the following description of the movement of the clip 44 into its position within the clip retaining cavity 105 in accordance with the preferred embodiment of the present invention is made soley to illustrate the position of the pusher member 140 and the clip 44 relative to the clip retaining cavity 105, and that jaw members 103 and 104 remain locked in a closed position as described above. Thus, by rotating handle 117 in a clockwise direction the clip moving means 106 is retracted so that the clip 44 can move from the clip cartridge 70 into the position shown in FIG.9. By next rotating the handle 117 downward, the slot follower 121 within slot 124 is caused to move in a counterclockwise direction, thereby urging the clip moving means 106 in a forward direction towards the clip retaining cavity 105. Simultaneously, the pusher member 140 moves the clip 44 towards the clip retaining cavity 105. The continued rotation of the handle 117 in a counterclockwise direction continues to urge the clip 44 towards the clip retaining cavity 105, as discussed above, until it reaches the same wherein the vas deferens 60 is contained within cavity 105 and clip 44, as shown in FIG. 10. The continued motion of the clip moving means 106 in the forward direction will cause the clip 44 to close around the vas deferens 60, in a manner similar to that set forth above with regard to the previously described embodiment. Thus, the forward movement of the pusher member 140 urges the upper end of the clip 44 against the camming surface 134. As the clip moving means 106 continues to move forward, the clip 44 begins to close against the camming surface 134, as can be seen in FIGS. 11–13. Further closure of the clip 44 is caused by the continued movement of the pusher member 140, whereby its boss member 140b bears against the camming surface 134, thus resulting in complete closure of the clip 44 around the vas deferens 60 as shown in FIG. 13. The surgeon can then slide selector switch 115 in a rearward direction so that tab 115g can matingly engage slot 117e, as noted above. In this position, handle 117 will be locked from further movement, and clip moving means 106 will be similarly locked in a forward position. As selector switch 115 can only be moved rearwardly when tab 115g is aligned with aperture 123 in slot 117e, the ability of the surgeon to move the switch in this direction will serve to indicate that the clip moving means 106 has been fully extended in a forward direction, and that clip 44 has been completely closed and locked around the vas deferens 60. As noted with regard to the previously described embodiment, the closing and locking of clip 44 is aided by means of recess 104a and camming surface 104b of lower jaw member 104, the details of which can be seen in FIGS. 9–13. As clip 44 closes, the foot 44a at the upper end thereof is urged toward lower jaw member 104, until surface 44b at the tip of foot 44a first bears against camming surface 104b. The continued closure of clip 44 by means of pusher member 140 will cause the foot 44a of clip 44 to turn inwardly as surface 44b bears against camming surface 104b. As closure proceeds, foot 44a will be urged into recess 104a where the same will be folded about end 44c of clip 44, so that the clip 44 becomes locked around the vas deferens as above.

As the selector switch 115 is engaged in the rearward position, removal of the device from the vas deferens 60 can be readily accomplished by rotating handle 118 in a counterclockwise direction, thereby opening the jaw members 103 and 104 and removing the device therefrom.

Another embodiment of the apparatus of the present invention is shown in FIGS. 24–27. In this embodiment a pair of jaw members 45 and 46 are interconnected by relative pivotable movement toward and away from each other. These jaw members 45 and 46 are adapted to hold an open clip 47 in operable position to enclose a target vessel 42. Clip 47 has a triangular configuration in this case, which is slightly different from the clips discussed above. Clip 47 is located between an upper fixed jaw member 45 and a lower pivotable jaw member 46 in the device shown therein. This lower jaw member 46 retains the bottom portion of clip 47 while the upper portion of the clip is held in operable position by the upper jaw member 45. The clip is inserted as part of a pivoting, scissor-like motion which is effected as ring 48 is moved downwardly. This action causes closure and locking of the clip 47 about the vas deferens 42. As can be seen in FIG. 24, a passage 49 is contained within the jaw member 45, and this passage 49 enables slide member 50 to have a telescoping movement within the lower jaw member 46. Slide member 50 has, at its distal end, a trocar obturator 51 which has a variety of functions including penetration and cutting through tissue and trapping a target vessel substantially similar in operation to those described above in connection with the preferred embodiment of the present invention.

The procedure used for implanting locking clips to effect percutaneous occlusion of the vas deferens with this embodiment of the invention involves insertion of the trocar obturator 51 in a forward direction by use of ring 52. Ring 52, in turn, is attached to the proximal end of the slide member 50 which has at its distal end trocar obturator 51. Thus, by moving the trocar obturator 51 in a forward direction tissue can be cut and the vas deferens exposed in a manner similar to that discussed above. The vas deferens 42 can be entrapped within the open clip 47, and once this occurs the lower jaw member 46 can be moved upwardly as ring 48 is moved downwardly, thereby effecting closure of the clip 47 about the vas deferens 42. Downward movement of the lower jaw member 46 thus leaves clip 47 implanted on the vas deferens as above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I CLAIM

1. Apparatus for implanting a closable locking clip to effect the percutaneous occlusion of a target vessel comprising first and second jaw members relatively pivotable between opened and closed positions, said first and second jaw members defining a clip-retaining cavity therebetween, said clip-retaining cavity having sufficient size to accommodate said locking clip therein, clip moving means for slidably moving said locking clip from a retracted position displaced from said clip-retaining cavity to an actuated position within said clip-retaining cavity, and camming means disposed within said clip-retaining cavity whereby upon said slidable movement of said locking clip from said retracted position to said actuated position said camming means causes at least a partial closure of said locking clip.

2. The apparatus of claim 1 including relative jaw pivot means for pivoting said first and second jaw members between said opened and closed positions.

3. The apparatus of claim 2 wherein said camming means is associated with one of said first and second jaw members, whereby upon said pivoting of said first and second jaw members into said closed position said camming means correspondingly pivots towards said other one of said first and second jaw members further facilitating said at least partial closure of said locking clip.

4. The apparatus of claim 3 wherein said one of said first and second jaw members includes an inner surface defining a portion of said clip-retaining cavity, and wherein said camming means comprises an angularly displaced wall surface of said inner surface of said one of said first and second jaw members.

5. The apparatus of claim 2 wherein said first and second-jaw members include first and second ends, respectively, said first ends of said first and second jaw members corresponding to said clip-retaining cavity, and said first and second jaw members being relatively pivotable about a fixed pivot point intermediate of said first and second ends of said first and second jaw members, and said relative jaw pivot means comprising moving means for moving said second ends of said first and second jaw members relative to each other so as to pivot said first and second jaw members about said fixed pivot point and thereby open and close said first ends of said first and second jaw members.

6. The apparatus of claim 5 wherein said moving means comprises slide means relatively slidable between a first position distal from said clip-retaining cavity and a second position relatively close to said clip-retaining cavity.

7. The apparatus of claim 6 wherein said slide means includes track means, and wherein said second end of one of said first and second jaw members includes track follower means whereby upon said sliding of said slide means between said first and second positions said track follower means follows said track means thereby moving said second ends of said first and second jaw members relative to each other.

8. The apparatus of claim 6 wherein said moving means further comprises handle means for sliding said slide means between said first and second positions.

9. The apparatus of claim 8 wherein said handle means comprises first and second pivotable handle members, said first and second pivotable handle members including a first end and a second end and being pivotable about a fixed pivot point intermediate of said first and second ends thereof, said first ends of said first and second pivotable handle members including gripping means and said second ends of said first and second pivotable handle members being in contact with said slide means.

10. The apparatus of claim 9 wherein said slide means includes slot means substantially transverse to the direction defined by movement of said slide means between said first and second positions, and wherein said second ends of said first and second pivotable handle members include first and second slot follower means, whereby upon said pivoting of said first and second pivotable handle members said first and second slot follower means travel within said slot means while causing said slide means to slide between said first and second positions.

11. The apparatus of claim 1 wherein said clip moving means comprises a slidable pusher member including a first end proximate to said clip-retaining cavity and a second end distal from said clip-retaining cavity.

12. The apparatus of claim 11 wherein said clip moving means includes pivotable handle means including a first end distal from said second end of said slidable pusher member and a second end proximate to said second end of said slidable pusher member and in contact therewith, said pivotable handle means being pivotable about a point intermediate of said first and second ends of said pivotable handle means whereby pivoting of said pivotable handle means results in longitudinal displacement of said slidable pusher member.

13. The apparatus of claim 12 wherein said slidable pusher member includes groove means substantially transverse to the direction defined by said longitudinal displacement of said slidable pusher member, and wherein said pivotable handle means includes, groove follower means.

14. The apparatus of claim 13 including relative jaw pivot means for pivoting said first and second jaw members between said open and closed positions.

15. The apparatus of claim 14 wherein said first and second jaw members include first and second ends, respectively, said first ends of said first and second jaw members corresponding to said clip-retaining cavity, and said first and second jaw members being relatively pivotable about a fixed pivot point intermediate of said first and second ends of said first and second jaw members, and said relative jaw pivot means comprising moving means for moving said second ends of said first and second jaw members relative to each other so as to pivot said first and second jaw members about said fixed pivot point and thereby open and close said first ends of said first and second jaw members.

16. The apparatus of claim 15 wherein said moving means comprises slide means relatively slidable between a first position distal from said clip-retaining cavity and a second position relatively close to said clip-retaining cavity.

17. The apparatus of claim 16 wherein said slide means includes track means, and wherein said second end of one of said first and second jaw members includes track follower means whereby upon said sliding of said slide means between said first and second positions said track follower means follows said track means thereby moving said second ends of said first and second jaw members relative to each other.

18. The apparatus of claim 16 wherein said moving means further comprises handle means for sliding said slide means between said first and second positions.

19. The apparatus of claim 18 wherein said handle means comprises first and second pivotable handle members, said first pivotable handle member comprising said clip moving means, and said first and second pivotable handle members including first ends and second ends, said first ends of said first and second pivotable handle members including gripping means and said second ends of said first and second pivotable handle members being capable of contacting said slide means.

20. The apparatus of claim 19 wherein said slide means includes slot means substantially transverse to the direction defined by movement of said slide means between said first and second positions, and wherein said second ends of said first and second pivotable handle members include first and second slot follower means, whereby upon said pivoting of said first and second pivotable handle members said first and second slot follower means travel within said slot means while causing said slide means to slide between said first and second positions, said first slot follower means comprising said groove follower means.

21. The apparatus of claim 20 wherein said slot means comprises first and second slot members associated with said first and second pivotable handle members, said first slot member including an aperture thereon, whereby said first slot follower means can exit said first slot member through said aperture, said first pivotable handle member being pivotable between a first position at one end of said first slot member and a second position at the other end of said first slot member, said second position being adjacent to said aperture, and said first pivotable handle member being pivotable into a third position whereby said first slot follower means pivots out of said aperture and remains in said groove means and thereby results in longitudinal displacement of said slidable pusher member.

22. The apparatus of claim 17 wherein said handle means comprises a pivotable handle member, said pivotable handle member including a first end and a second end, said first end of said pivotable handle member including gripping means and said second end of said pivotable handle member being capable of contacting said slide means.

23. The apparatus of claim 22 wherein said slide means includes slot means substantially transverse to the direction defined by movement of said slide means between said first and second positions, and wherein said second end of said pivotable handle member includes slot follower means, whereby upon said pivoting of said pivotable handle member said slot follower means travels within said slot means while causing said slide means to slide between said first and second positions.

24. Apparatus for implanting a closeable locking clip to effect the percutaneous occulsion of a target vessel comprising first and second jaw members relatively pivotable between open and closed positions, said first and second jaw members defining a clip-retaining cavity therebetween, said clip-retaining cavity having sufficient size to accommodate said locking clip therein, clip moving means for slidably moving said locking clip from a retracted position displaced from said clip-retaining cavity to an actuated position within said clip-retaining cavity, switch means slidable between a first position and a second position, said first position locking said first and second jaw members in said closed position, said second position locking said clip moving means from longitudinal displacement, and camming means disposed within said clip-retaining cavity whereby upon said slidable movement of said locking clip from said retracted position to said actuated position said camming means causes at least a partial closure of said locking clip.

25. The apparatus of claim 24 including relative jaw pivot means for pivoting said first and second jaw members between said open and closed positions.

26. The apparatus of claim 25 wherein said camming means is associated with one of said first and second jaw members, whereby upon said pivoting of said first and second jaw members into said closed position said camming means correspondingly pivots towards said other one of said first and second jaw members further facilitating said at least partial closure of said locking clip.

27. The apparatus of claim 26 wherein said one of said first and second jaw members includes an inner surface defining a portion of said clip-retaining cavity, and wherein said camming means comprises an angularly displaced wall surface of said inner surface of said one said first and second jaw members.

28. The apparatus of claim 25 wherein said first and second jaw members include first and second ends, respectively, said first ends of said first and second jaw members corresponding to said clip-retaining cavity, and said first and second jaw members being relatively pivotable about a fixed pivot point intermediate of said first and second ends of said first and second jaw members, and said relative jaw pivot means comprising moving means for moving said second ends of said first and second jaw members relative to each other so as to pivot said first and second jaw members about said fixed pivot point and thereby open and close said first ends of said first and second jaw. members.

29. The apparatus of claim 28 wherein said moving means comprises slide means relatively slidable between a first position distal from said clip-retaining cavity and a second position relatively close to said clip-retaining cavity.

30. The apparatus of claim 29 wherein said slide means includes track means, an wherein said second end of one of said first and second jaw members includes track follower means whereby upon said sliding of said slide means between said first and second positions said track follower means follows said track means thereby moving said second ends of said first and second jaw members relative to each other.

31. The apparatus of claim 29 wherein said moving means further comprises handle means for sliding said slide means between said first and second positions.

32. The apparatus of claim 31 wherein said handle means comprises a first pivotable handle member, said first pivotable handle member including a first end and a second end and being pivotable about a fixed pivot point intermediate of said first and second end thereof, said first end of said first pivotable handle member including gripping means and said second end of said first pivotable handle member being in contact with said slide means.

33. The apparatus of claim 32 wherein said switch means includes hook means for operative engagement with said second end of said pivotable handle member to lock said slide means in said second position relatively close to said clip-retaining cavity.

34. The apparatus of claim 33 wherein said slide means includes slot means substantially transverse to the direction defined by movement of said slide means between said first and second positions, and wherein said second end of said first pivotable handle member includes slot follower means, whereby upon said pivoting of said first pivotable handle member said slot follower means travels within said slot means while causing said slide means to slide between said first and second positions.

35. The apparatus of claim 24 wherein said clip moving means comprises a slidable pusher member including a first end proximate to said clip-retaining cavity and a second end distal from said clipretaining cavity.

36. The apparatus of claim 35 wherein said clip moving means includes pivotable handle means including a first end distal from said second end of said slidable pusher member and a second end proximate to said second end of said slidable pusher member and in contact therewith, said pivotable handle means being pivotable about a fixed pivot point intermediate of said first and second ends of said pivotable handle means whereby pivoting of said pivotable handle means results in longitudinal displacement of said slidable pusher member.

37. The apparatus of claim 36 wherein said switch means includes tab means for operative engagement with said second end of said pivotable handle means to lock said slidable pusher member from longitudinal displacement.

38. The apparatus of claim 37 wherein said slidable pusher member includes means substantially transverse to the direction defined by said longitudinal displacement of said slidable pusher member, and wherein said pivotable handle means includes groove follower means.

39. The apparatus of claim 35 including for pivoting said first and second jaw members between said open and closed positions.

40. The apparatus of claim 39 wherein said first and second jaw members include first and second ends, respectively, said first ends of said first and second jaw members corresponding to said clip-retaining cavity, and said first and second jaw members being relatively pivotable about a fixed pivot point intermediate of said first and second ends of said first and second jaw members, and said relative jaw pivot means comprising moving means for from moving said second ends of said first and second jaw members relative to each other so as to pivot said first and second jaw members about said fixed pivot point and thereby open and close said first ends of said first and second jaw members.

41. The apparatus of claim 40 wherein said moving means comprises slide means relatively slidable between a first position distal from said clip-retaining cavity and a second position relatively close to said clip-retaining cavity.

42. The apparatus of claim 41 wherein said first position of said switch means locks said slide means in said second position relatively close to said clip-retaining cavity.

43. The apparatus of claim 42 wherein said slide means includes track means, and wherein said second end of one of said first and second jaw members includes track follower means whereby upon said sliding of said slide means between said first and second positions said track follower means follows said track means thereby moving said second ends of said first and second jaw members relative to each other.

44. The apparatus of claim 42 wherein said moving means further comprises handle means for sliding said slide means between said first and second positions.

45. The apparatus of claim 44 wherein said handle means comprises a pivotable handle member, said pivotable handle member including a first end and a second end, said first end of said pivotable handle member including gripping means and said second end of said pivotable handle member being capable of contacting said slide means.

46. The apparatus of claim 45 wherein said switch means includes hook means for operative engagement with said second end of said pivotable handle member to lock said slide means in said second position relatively close to said clip-retaining cavity.

47. The apparatus of claim 46 wherein said slide means includes slot means substantially transverse to the direction defined by movement of said slide means between said first and second positions, and wherein said second end said pivotable handle member includes slot follower means, whereby upon said pivoting of said pivotable handle member said slot follower means travels within said slot means while causing said slide means to slide between said first and second positions.

* * * * *

UNITED STATES PATENT AND TRADEMARK OFFICE
CERTIFICATE OF CORRECTION

PATENT NO. : 4,967,949

DATED : November 6, 1990

INVENTOR(S) : Jeffrey J. Sandhaus

It is certified that error appears in the above-identified patent and that said Letters Patent is hereby corrected as shown below:

Column 5, line 9, delete "side".

Column 6, line 60, following "FIG." (first occurrence), insert --1--.

Signed and Sealed this

Nineteenth Day of May, 1992

Attest:

DOUGLAS B. COMER

*Attesting Officer*   *Acting Commissioner of Patents and Trademarks*